United States Patent [19]

Rammler

[11] 4,123,614

[45] Oct. 31, 1978

[54] NOVEL ASSAY REAGENTS

[75] Inventor: David H. Rammler, Palo Alto, Calif.

[73] Assignee: Syntex (U.S.A.) Inc., Palo Alto, Calif.

[21] Appl. No.: 733,638

[22] Filed: Oct. 18, 1976

Related U.S. Application Data

[62] Division of Ser. No. 509,528, Sep. 26, 1974, abandoned, which is a division of Ser. No. 225,342, Feb. 10, 1972, Pat. No. 3,880,934.

[51] Int. Cl.$^2$ .............................................. C07C 79/22
[52] U.S. Cl. .............................. 560/254; 195/103.5 C; 195/103.5 R; 260/335; 260/404; 260/404.5; 260/455 R; 260/457; 260/551 P; 260/562 A; 260/570.7; 260/613 D; 260/926; 260/929; 260/944; 260/951; 424/2; 424/7; 424/8; 424/12; 560/29; 560/32; 560/38; 560/40; 560/41; 560/137; 560/173; 560/251
[58] Field of Search ................ 260/404, 488 CD, 490, 260/404.5; 560/254

[56] References Cited

U.S. PATENT DOCUMENTS

| 2,291,527 | 7/1942 | Bruson et al. ................ 260/488 CD |
| 3,419,620 | 12/1968 | Becher et al. ................ 260/488 CD |

OTHER PUBLICATIONS

Chem. Abstracts: 41:5484i, 5485a.

*Primary Examiner*—Vivian Garner
*Attorney, Agent, or Firm*—Tom M. Moran; Walter H. Dreger

[57] ABSTRACT

The present invention relates to novel assay reagents, their composition, methods of preparation, and use in the detection and measurement of various biological systems and/or components, e.g. enzymes, antibodies, antigens, and periodate concentration. This invention in its basic form utilizes a class of compounds having, inter alia., a backbone chain, an indicator group, and vicinal oxidizable groups.

3 Claims, No Drawings

NOVEL ASSAY REAGENTS

This is a division of application U.S. Pat. application Ser. No. 509,528 filed September 26, 1974, Now abandoned, which in turn is a division of U.S. Pat. application Ser. No. 509,528 filed September 26, 1974, now aban- 3,880,934 issued Apr. 29, 1975.

The present invention relates to novel assay reagents, their composition, methods of preparation, and use in the detection and measurement of various biological systems and/or components. In particular, the novel assay reagents of the present invention are useful, inter alia., in the detection and measurement of enzyme activity and the concentration of various antigen and antibody substances. These reagents are ideally suited to amplification so as to be useful in the detection of relatively small concentrations of the measured component.

The present invention operates generally by reaction of a reagent with a component to be detected and measured, such as an enzyme, whereby the reagent is chemically altered to a form readily suited to convenient measurement by spectrophotometric means. Thus, the amount of chemically altered reagent formed is directly proportional to the amount of the biochemical component sought to be measured.

In the assay of enzyme activity, a suitable substrate reagent is mixed with an excess of the biological materials containing the enzyme to be measured. The enzyme reacts with the reagent, such as by hydrolyzing a suitable ester group, to give a product which can be treated, in accordance herewith, to give an equivalent (based upon the amount of enzyme present) amount of fluorescent or colored indicator which can be measured accordingly. Thus, the concentration of the indicator group is equivalent to the concentration of altered reagent whose concentration is a function of the enzyme activity in the unknown.

Immunological measurements can be made using the reagents hereof in the following manner. The reagent can be chemically associated or coupled with an antigen. The resultant antigen-reagent compound is then added to its specific antibody in such a way so as to saturate the antigen binding sites on the antibody. Upon the addition of biological material containing the antigen to be measured, the antigen-reagent compound is displaced from the antibody by the antigen contained in the biological material. The displaced antigen-reagent compound can be measured by chemical cleavage of the indicator group. The amount cleaved is therefore proportional to the amount of antigen in the biological material capable of displacing the antigenreagent compound.

In a similar manner, antibody can be measured using reagent-antibody compounds.

In the alternative, the reagent can be attached to the antibody in such a way so as not to block its antigen binding sites. Antigen is then added and an antibody-antigen complex is prepared. The residual non-reactive antibody is removed by appropriate methods, and the remaining antibody reagent-antigen complex is a measure of the amount of antigen present. This amount can be evaluated by appropriate cleavage of the indicator group thereof, the amount of which is proportional to the amount of antibody-reagent antigen complex.

The amount of periodate in a system which is capable of releasing a measurable amount of indicator from a suitable reagent hereof, provides a direct determination of the periodate concentration.

The method by which the altered reagent is measured constitutes the first, principal aspect of the present invention. This aspect involves a method which comprises treating a compound selected from those of the formula:

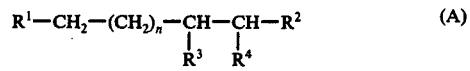

wherein, $n$ is 0 or 1;

$R^1$ is an indicator group;

$R^2$ is hydrogen, a coupled antibody or antigen;

$R^3$ is hydroxy; and $R^4$ is hydroxy, amino, or mercapto;

with an oxidizing agent capable of cleaving the bond of the carbons bearing the $R^3$ and $R^4$ substituents, followed by elimination of the indicator group ($R^1$).

In the present context, the term "indicator group" refers to a group which, in its free form when released from the parent compound, is fluorescent and/or emits electromagnetic vibrations in the wavelengths of the visible spectrum, i.e. from about 300 to about 800 m$\mu$, or which is a radioisotope. The scope of this term is inclusive of the common indicators and thus includes those chromaphore and fluorophore groups which are known in the art. Representative groups are p-nitrophenoxy, o,p-dinitrophenoxy, fluorescein, methoxyfluorescein, o-amino benzoate, and coumarins. Also useful are phenols or aromatic compounds iodinated with $I^{125}$ or labelled with $C^{14}$ carbon. Preferred indicator groups are p-nitrophenoxy, o,p-dinitrophenoxy, fluorescein, methoxyfluorescein, the coumarins, and 2,4-diiodo($I^{125}$)-phenoxy.

In the present specification and claims, the term "coupled antibody or antigen" is intended to include an "antibody or antigen group" together with a means of being coupled to the terminal carbon atom of the reagent backbone chain, whether said means is a direct chemical bond or a specific coupling group. Suitable coupling groups include ester or amido groups of the partial formula (see Formula A above):

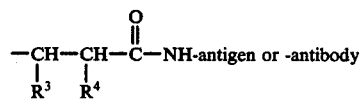

or amine groups of the partial formula (see Formula A above):

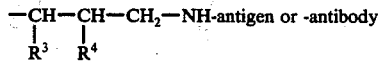

The term "antibody or antigen group" is defined, for the purposes hereof, as, in the case of antigens, biological materials such as hormones, insulin, steroids, or peptides, e.g. testosterone or chorionic gonadotropin, and also small antigens such as drugs, e.g. opiates and certain bacteria, e.g. gonorrhea (Neisseria gonorrhoeae). In the case of antibodies are included the natural blood antibodies such as those for certain viruses, e.g. hepatitis, and those for certain bacteria, e.g. tubercle bacillus.

The oxidation and elimination can be conducted simultaneously or as separate steps. The oxidation is effected with suitable oxidizing agents which include sodium metaperiodate and its oxidizing meta stable components; lead tetraacetate; and certain bismuthates, e.g. sodium bismuthate. Preferred is periodate ion, in the form of its soluble salts such as the sodium, potassium, or amine salts.

The elimination is effected with suitable base reagents which include, in the presence of the oxidation agent, aliphatic primary or secondary amines, e.g. methylamine, ethylamine, cyclohexylamine, diethylamine, and so forth, and certain aromatic amines such as aniline. There can also be employed other bases such as the sodium or potassium hydroxides, carbonates, or bicarbonates.

One useful method by which the oxidation and elimination can be conducted as one step (oxidative elimination) involves treating the reagent with excess oxidizing agent together with base as listed above. The oxidation and elimination reactions are conducted in any convenient fashion, at temperatures ranging from about 5° C. to about 100° C. and for a period of time ranging from about 1 minute to about 25 minutes.

The reaction consumes the reactants upon the basis of one mole each of oxidizing agent per mole of substrate, however, with the use of amine, greater amounts of oxidizing agent are used. Although the reactions can be conducted using any proportions of reactants, in the preferred embodiments, from about five to about ten moles of oxidizing agent and from about 10 to about 100 moles of base are employed per mole of appropriate reactant.

The method of the first aspect of the present invention can be further illustrated and described as follows in Sequence A:

base, e.g. sodium hydroxide, the indicator groups (3) and (5) are eliminated.

Alternatively, a compound of (1) is treated with amine in the presence of oxidizing agent, giving (7) and (8) or (9) and (10), if the solution is slightly basic.

The present invention, in a second aspect, relates to a method useful for enzyme measurements or the detection and measurement of (hydrolytic) enzyme activity. This method comprises hydrolyzing a compound selected from those of the formula:

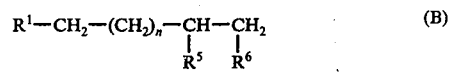

wherein each of $n$ and $R^1$ is as defined above; and $R^5$ is hydroxy or an enzymatically hydrolyzable group; and $R^6$ is hydroxy, amino, mercapto, or an enzymatically hydrolyzable group; at least one of $R^5$ and $R^6$ being said enzymatically hydrolyzable group; with a suitable enzyme to give a compound selected from those of the following formula:

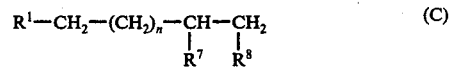

wherein each of $n$ and $R^1$ is as defined above; and $R^7$ is hydroxy; and $R^8$ is hydroxy, amino, or mercapto; and treating a compound selected from those of Formula (C) with an oxidizing agent capable of cleaving the bond of the carbons bearing the $R^7$ and $R^8$ substituents, followed by elimination of the indicator group ($R^1$).

In the present context, the term "enzymatically hy-

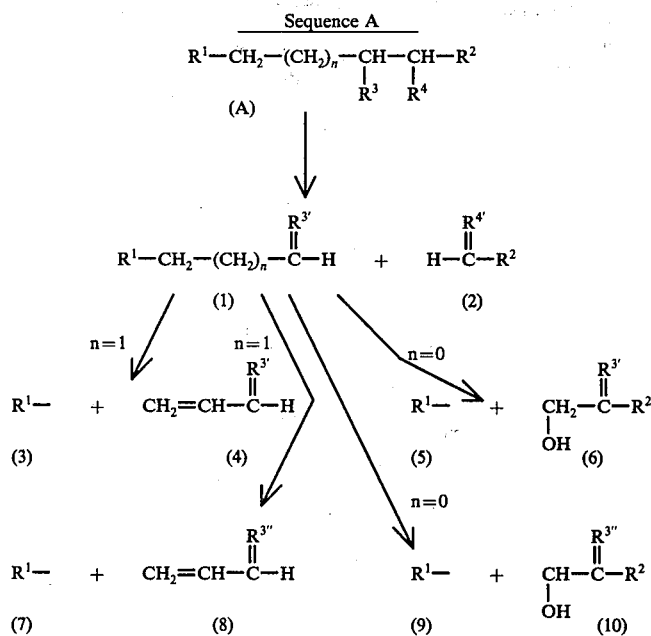

wherein each of $R^1$, $R^2$, $R^3$, $R^4$ and $n$ is as defined above; $R^{3'}$ is oxo; $R^{4'}$ is oxo, imino, or thioxo; and $R^{3''}$ is an imino group.

With reference to the above Sequence A, a compound of Formula A is treated with oxidizing agent, such as periodate, as described above, to provide compounds (1) and (2). Upon treatment of (1) with strong drolyzable group" refers to a group which can be cleaved (hydrolyzed) by hydrolytic enzymes such as the alkaline and acid phosphomonoesterases, sulfatases, esterases, peptidases, proteinases, carbohydrases, and ureases. In general, these enzymatically hydrolyzable groups can be selected from (1) esters including the phosphomonoesters and phosphodiesters of phosphoric acid and aliphatic, aromatic, and aralkyl carboxylic esters and sulfuric acid mono and diesters and esters of reduced substances such as phoshpite and sulfinic acids;

(2) amides including amides of aliphatic, aromatic, aralkyl, amino, peptide, and protein acids and amides of inorganic acids such as phosphoramidic acids; and (3) glycosides including the glycosides of pentoses and hexoses.

Particularly useful enzymatically hydroyzable groups are, in the ester series, the phosphomonoester of the formula:

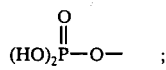

the carboxylic esters of the formula:

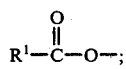

wherein $R^1$ is alkyl of 1 to 18 carbon atoms, preferably straight chain, or an amino acid moiety, such as glycine, lycine, phenylalanine, and the like; and the sulfuric acid monoester of the formula:

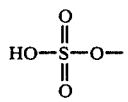

In the amide series, particularly useful enzymatically hydrolyzable groups are the organic acids of the formula:

wherein $R''$ is an amino acid moiety, such as those listed above, or a peptide moiety such as leucylleucine or glycyllysine or larger tri, tetra, or penta peptides and the inorganic amide of the formula, useful for phosphoroamidases:

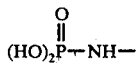

In those instances wherein two enzymatically hydrolyzable groups are present, they can be different or, preferably, the same so long as each is susceptible to enzyme hydrolysis. In addition, a single compound ester can be present such as a phosphodiester which must be hydrolyzed in two stages by two different enzymes, first a diesterase followed by a phosphomonoesterase. This flexibility permits the detection and measurement of one or two different enzymes in a biological system.

The particular enzyme which is capable of hydrolyzing a particular enzymatically hydrolyzable group is, in general, within the skill of the art. For example, the alkaline and acid phosphomonoesterase enzymes are hydrolytic toward the various phosphorus acid ester and amide enzymatically hydrolyzable groups. Similarly, the esterases are hydrolytic to the various carboxylic acid esters, the sulfatases are hydrolytic to the various sulfuric acid esters, the protein enzymes are hydrolytic to ester or amide groups and the ureases to the substituted urea groups.

These hydrolytic enzymes are present and can be detected and measured in various biological fluids such as serum, urine, and blood and in biological material such as tissue, cells, (mammalian, protozoan, plant, and bacterial) and in extracts of these materials. In general, the reagents hereof can be used with any source of material which has enzymatic activity and which can utilize these compounds as substrates in the detection and measurement of enzymatic activity.

In accordance with this aspect of the present invention, a reagent compound selected from those represented by Formula (B) above is contacted with a biological material having enzymatic activity to prepare the hydrolyzed derivative of said compound (B), that is compound (C), and oxidizing said hydrolyzed derivative (C) followed by hydrolysis of the indicator group, as defined above.

The hydrolysis can be conducted in any convenient fashion, at temperatures ranging from about 20° to about 40° C. and for a period of time ranging from about 1 minute to about 24 hours, and at a pH and salt concentration suitable for the enzyme activity. For long assays, the pH is generally kept at about 7 to 8.

The free indicator group is measured in intensity spectrophotometrically or radiographically to determine the extent or amount of enzyme activity (hydrolysis) provided. Thus, the amount of enzymatic activity is reflected by the extent of the hydrolysis of the enzymatically hydrolyzable group, the latter being measured by the intensity of (electromagnetic or isotope) radiation of the indicator group which is removed or cleaved only from that portion of reagent (B) which has been enzymatically hydrolyzed, that is, compound (C).

By use of standardized aliquots of biological material together with mathematically equivalent measurement of indicator group, the relative level of enzyme activity detected and measured can be calculated. This determination of enzyme activity levels in a particular organism is clinically useful in diagnosing conditions or diseases which cause and reflect improper enzyme level balance.

For example, serum levels of certain enzymes which are above or below normal limits often indicate serious conditions or diseases such as hepatic, myocardial, pancreatic, and prostatic diseases. Thus, in the case of increased alkaline phosphatase levels, obstructive jaundice, biliary cirrhosis, and chloangiolitic hepatitis may be diagnosed and, in the case of decreased alkaline phosphatase levels, hypophosphatasia and malnutrition may be diagnosed. Similarly, increased acid phosphate levels may be clinically indicative of prostate carcinoma and metastases therefrom. A knowledge of serum lipase versus serum amylase levels is clinically useful in the diagnosis of various pancreatic diseases and conditions. A study of serum levels of CPK, GOT, LDH, and GPT has a direct use in the indication of myocardial infarction. The number of uses for clinical diagnosis are large and are listed in standard handbooks of clinical medicine.

The present invention, in a third aspect, relates to a method useful for immunological measurements, e.g. the detection and measurement of various antigen and antibody substances. This method comprises treating a compound selected from those of the formula:

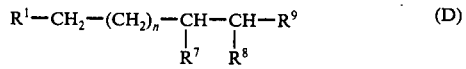

wherein each of $R^1$, $n$, $R^7$, and $R^8$ is as defined above and $R^9$ is a coupled antibody or antigen, as defined above, with an oxidizing agent capable of cleaving the bond of the carbons bearing the $R^7$ and $R^8$ substituents, followed by elimination of the indicator group ($R^1$). The oxidation and elimination reactions are conducted as described above. p Immunological measurements utilizing the above method can be conducted in several ways. In one method, the antigen-reagent complex is allowed to attach to the binding sites on its antibody. The specimen of biological fluid containing the antigen to be measured is mixed in the antigen-reagent complex. The amount of the antigen in the biological fluid is measured indirectly by determining the amount of antigen-reagent it displaces from the antibody. This reagent is determined by its indicator after treatment as above described.

Another, more direct, method proceeds by allowing the antibody to react with the biological fluid containing the antigen to be measured. After saturation of the antibody with the unknown antigen, the antigen reagent complex is added. The binding sites not used by the unknown antigen are now taken up with the reagent antigen. The amount of antigen-reagent which binds with the antibody in the absence of the unknown, less the amount which binds after reaction with the unknown, is the amount of antigen present in the unknown. Here again the antigen-reagent complex is determined in a subsequent chemical reaction, as described above.

Antibody can also be labeled with the reagent. Here the antibody is saturated with the unknown antigen. The antibody which is not saturated with antigen is removed from the reaction by absorbing it on to an antigen-solid matrix support. This leaves only the agnet-antibody with its unknown antigen in solution. This substance is determined using the chemical method, as described previously.

In this method, an antibody or antigen is immobilized on a solid matrix carrier. Polymers used as carriers can be chosen from those which will physically absorb the antibody or antigen, such as charcoal, clays and glass beads. Other polymer carriers can be chosen which chemically couple the antibody or antigen, such as polyvinyl benzene derivatives, arylamines, carboxylic acids and sulforic acids; polyethylene derivatives, e.g. polyacrylic acids; cellulose and its derivatives; fibroin; wool; polypeptides; precipitated proteins; and red blood cell stroma. Other substances which can be chosen as carriers include proteins or other substances entrapped in an organic polymer matrix. The immobilization of the antibody or antigen is conducted by methods known in the art, such as coupling through an azo link, isothiocyanate group, or nonspecific absorption, as described, for example, by Axen et al., *Acta. Chem. Scand.* 18, No. 9, 2193 (1964), Axen et al., *Nature* 210, 367 (1966), Gurevich et al., *Biokhimiya*, 26, No. 5, 934 (1961), Onove et al., *Immunochemistry*, Pergamon Press, 2, 181 (1965), Surinov et al., *Biokhimiya*, 31, No. 2, 387 (1966), Weliky et al., *Immunochemistry*, Pergamon Press, 2, 323 (1965), and the various references cited therein, which are hereby incorporated by reference.

In this way, a carrier is formed having bound antibody or antigen in an amount calculatable to a known binding capacity. After the immobilization has taken place, an unknown test specimen containing antigen (or antibody) specific for the immobilized antibody (or antigen) is passed through the matrix. The antigen (or antibody) contained in the specimen complexes with the complementary antibody (or antigen) immobilized on the matrix.

A predetermined amount of a compound of Formula (D) wherein $R^9$ is the antigen (or antibody) specific for the immobilized antibody (or antigen) or, in other words, identical to the antigen (or antibody) contained in the unknown, is then contacted with the thus treated matrix. The remaining non-bonded sites on the matrix are thus utilized to complex with a fraction of the compound of Formula (D) and the remaining fraction of compound (D) is recoverable and can be measured spectrophotometrically, as described above. Simple calculation from the known binding capacity of the matrix, the amount of reagent (compound D) employed, and the amount recovered (not complexed), provides a determination of the amount of antigen (or antibody) present in the unknown test specimen. The amount of indicator group measured is a function of the amount of antigen (or antibody) tested.

Thus, for the convenience of simplicity, if four antibody molecules are immobilized on a matrix and treated with a test specimen, e.g. urine, containing three antigens specific therefor, one antibody site remains. Five molecules of a compound of Formula (D) wherein $R^9$ is the same specific antigen as present in the test specimen is then contacted with the treated matrix. One molecule will bind with the remaining site and the other four, when treated as described above, yields four indicator groups which are intensity compared. Simple calculation, i.e. 4-(5-4)=3, determines the concentration of antigen contained in the test specimen.

An alternative manner hereof for immunological measurements utilizes a known amount of a complex of a compound of Formula (D) with an antibody (or antigen) specific for the antigen (or antibody) group ($R^9$) of the compound employed. A test specimen containing an unknown concentration of the antigen (or antibody) identical with group ($R^9$) is contacted with said complex whereby the test specimen antigen (or antibody) displaces compound (D). The displaced material is then treated and comparison measured, as described above, to provide a direct determination of the unknown antigen (or antibody) concentration.

Thus, for the convenience of simplicity, if five molecules of a specific morphine antibody complex with a compound of Formula (D) wherein $R^9$ is a morphine residue, is contacted with a test specimen, e.g. urine, containing four molecules or morphine; the urine morphine will displace four molecules of the compound of Formula (D) which, when treated and comparison measured as described above, provides a direct determination of morphine concentration in the specimen unknown.

Similar measurements of, e.g. chorionic gonadotropin provides a simple, direct and accurate diagnosis of pregnancy in the female human.

Test materials containing unknown concentrations of antibody or antigen may be obtained from a variety of sources. For example, various biological fluids, such as described above, can be tested for the presence of specific substances. In general, the reagents hereof can be used with any material source which contains a specific antibody or antigen and which can utilize these compounds as substrates in the detection and measurement of said antibodies and/or antigens.

The reagents and method hereof are also useful for the detection and measurement of periodate concentration in a given system. By contacting a known amount of a compound according to Formula (A) with an unknown periodate followed by elimination of the indicator group, as defined above, a direct measurement of the periodate concentration is provided. The utility of this method is provided by an accurate measurement of unused and, therefore, used periodate in a system in which periodate is being used as a reactant, for example, in the detection of glycol concentration of carbohydrate or carbohydrate containing biological materials.

The reagents and method hereof are also useful to measure oxidative enzyme activity, such as alcohol dehydrogenase, in a given system. In this method, a compound of Formula (A), wherein each of $R^3$ and $R^4$ is hydroxy and $R^2$ is hydrogen, is contacted with an unknown oxidative enzyme specimen, whereby the corresponding terminal aldehyde compound is prepared. Elimination of the indicator group, as described above, of the thus-prepared aldehyde portion provides a direct measurement of said enzyme concentration. Such enzymes are useful biologically and variances in concentration thereof may be indicative of certain metabolic disorders, for example, liver diseases.

As mentioned above, the reagents hereof are ideally suited to amplification whereby minute concentrations of unknown material can be measured. As one example, multiple compounds of Formula (B) can be linked together by means of bifunctional ester groups ($R^5$ and/or $R^6$). As few as two hydrolytic enzyme molecules are capable of cleaving each ester bond releasing the several molecules of compound (C), which can be treated as described above. Thus provided is a means by which low concentrations of component antibody or antigen can be detected and spectrophotometrically measured. Thus, a compound of Formula (E) below can be prepared and treated with non-specific phosphodiesterase and a phosphomonoesterase to give the compounds of Formula (F) below, which can be treated as above described, to give the free indicator groups ($R^1$) which are measured spectrophotometrically:

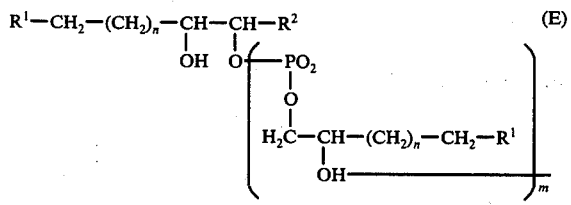
(E)

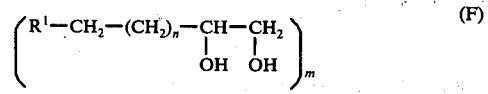
(F)

-continued
+

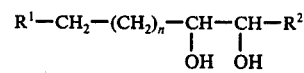

wherein $m$ is a positive integer.

The present invention, in a fourth aspect, relates to the novel compounds hereof selected from those of Formulas (A), (B), (C), and (D) above, as represented by the following Formula (G):

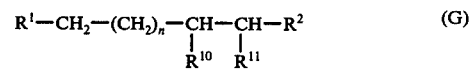

wherein $R^1$ is an indicator group; $n$ is 0 or 1; $R^2$ is hydrogen, a coupled antibody or antigen; $R^{10}$ is hydroxy or an enzymatic hydrolyzable group; and $R^{11}$ is hydroxy, amino, mercapto, or an enzymatically hydrolyzable group; provided that when $R^2$ is hydrogen and each of $R^{10}$ and $R^{11}$ is other than an enzymatically hydrolyzable group, then $n$ is 1. Preferred of the novel compounds of Formula (G) are those wherein $n=1$ and those thereof wherein $R^1$ is 4-nitrophenyloxy or 2,4-dinitrophenyloxy or fluorescein, or methoxyfluorescein and those thereof wherein each of $R^{10}$ and $R^{11}$ is hydroxy and those thereof wherein $R^2$ is hydrogen of the respective Formulas:

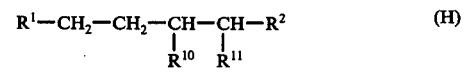
(H)

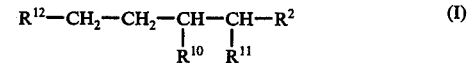
(I)

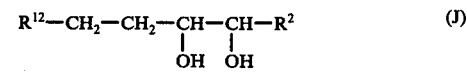
(J)

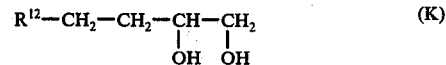
(K)

wherein $R^{12}$ is 4-nitrophenyloxy, 2,4-dinitrophenyloxy, fluorescein or methoxyfluorescein. Particularly preferred are those compounds of Formulas (I), (J), and (K) above wherein $R^{12}$ is 4-nitrophenyloxy and those of Formula (H) wherein $R^1$ is 4-nitrophenyloxy.

The reagents hereof can be suitably formulated in a stable buffer system by means of conventional methods known in the art. Representative pH stable buffers include sodium acetate (0.1M, pH 4.5), sodium phosphate (0.1M, pH 7.5), triethanolamine hydrochloride (0.1M, pH 8.5), and the like. Buffers which consume periodate, such as tris-(hydroxymethyl)aminomethane, are to be avoided.

The compounds of the present invention are prepared according to the following reaction Sequence B:

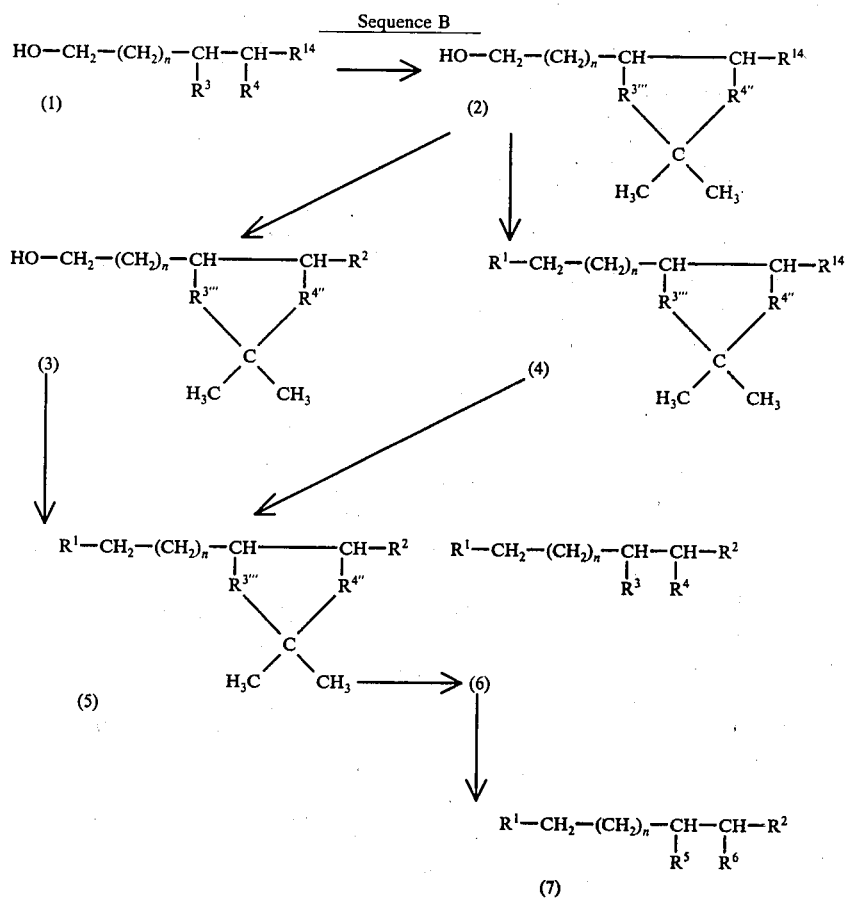

Sequence B wherein each of $n$, $R^2$, $R^3$, $R^4$, $R^5$, and $R^6$ is as above defined; $R^{3'''}$ is oxy; and $R^{4''}$ is oxy, sec-amino, or thio; and $R^{14}$ is hydrogen or a coupled antibody or antigen.

With reference to the above depicted sequence, the protective acetal (2) of compound (1) is prepared by reaction with 2,2-dimethoxypropane — see *J. Amer. Chem. Soc.* 83, 756 (1961) and *J. Org. Chem.* 26, 2863 (1961). Compound (2) is then reacted, if desired, with a suitable antibody or antigen group reagent to form those compounds of Formula (3) wherein $R^2$ is a coupled antibody or antigen. The free hydroxy group of compound (3) is then reacted with the desired indicator halide in the presence of a tertiary amine such as triethylamine, pyridine, and the like, in accordance with the conventional method as set forth by Wagner and Zook *Synthetic Organic Chemistry*, John Wiley and Son, New York, 1953, page 227 and the references cited therein, to give compound (5). This compound is then hydrolyzed with acid to cleave the acetal group and provide compounds (6) which are converted to compounds (7) upon conventional esterification.

Alternatively, the indicator group ($R^1$) can be introduced (compound 4) prior to introduction of the antibody or antigen group (compound 5), if desired.

Alternatively, certain of the compounds of the present invention are prepared in accordance with the following reaction sequences:

Sequence C

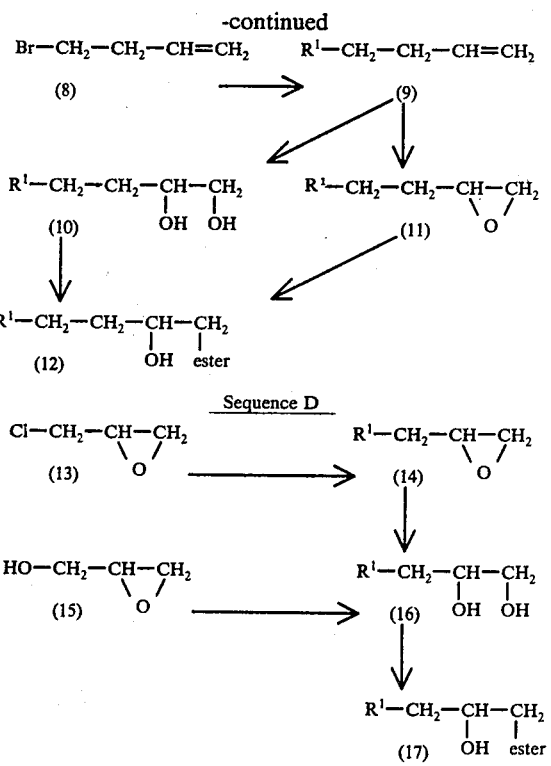

wherein $R^1$ is as above defined and ester is an enzymatically hydrolyzable ester as defined above.

With reference to Sequence C, an indicator group is added as a replacement of the bromo group on 4-bromo-1-butene to give (9). By treatment of the thus prepared compound with performic acid, the corresponding 1,2-butanediol (10) is prepared which can be esterified in accordance with the foregoing procedures to prepare the product (12). Alternatively, the 1,2-butene compound (9) can be treated with m-chloroperbenzoic acid to form the corresponding 1,2-epoxide (11) followed by opening the epoxide with ester anion to prepare the corresponding compounds (12).

With reference to Sequence D, epichlorohydrin (13) is reacted as described above to introduce $R^1$ followed by treatment with base followed by reaction with aqueous sodium hydroxide yields the corresponding 1,2-epoxypropane (14). The epoxide of this compound can be hydrolyzed by dilute acid to yield the corresponding diol (16) which can be esterified as set forth above to prepare the primary monoesters (17).

Alternatively, the ring opening of glycidol (15) with an indicator reagent as described above, in base yields the corresponding 1,2-propanediol (16) which is esterified (17), as described above.

Certain of the compounds of formula (6) above can also be prepared in accordance with the procedure of Petrow et al., *J. Pharmacy and Pharmacology* 5, 359 (1953). This method involves forming the epoxide compound containing an indicator group and treating the latter with aqueous ethanolic ammonium hydroxide to give the vicinal hydroxy-amino compounds. These are then esterified as described above.

The following examples serve to illustrate further the manner by which the present invention can be practiced.

The following series of examples illustrate the method by which the compounds of the present invention can be prepared.

EXAMPLE 1

A mixture of 4-nitrophenol (0.6 mole, 82.3 grams), epichlorohydrin (1.8 mole, 167 g.) and piperidene (3 ml.) is stirred at 100° C. for 17 hours. The solution is evaporated and to the residue is added sodium hydroxide (2 mole) in 500 ml. of water. After 24 hours of stirring, the solution is extracted with chloroform. After washing with dilute sodium hydroxide, the dried chloroform solution is evaporated yielding 3-(4-nitrophenyloxy)-1,2-epoxypropane. A solution of the epoxide (1.0 g.) in 50% aqueous acetic acid (15 ml.) is heated at 90° C. for five hours and then evaporated and chromatographed on silica acid plates (chloroform-methanol 9:1). The band with an $R_f$ of about 0.5 is eluted and crystallized from chloroform and ethyl acetate to yield 1,2-dihydroxy-3-(4-nitrophenyloxy)-propane.

EXAMPLE 2

1-Nitrophenol (2.6 grams; 19 mmole) is added to a mixture of 2,3-epoxypropanol (1.16 g; 15.6 mmole), anhydrous methanol (10 ml.) and sodium methylate (1.0 g.). After five hours under reflux, the solvent is evaporated and the residue chromatographed on preparative silicic acid plates using chloroform-methanol (9:1) to yield 1,2-dihydroxy-3-(4-nitrophenyloxy)-propane which may be crystallized from chloroform-ethyl acetate. In a similar manner, 1,2-dihydroxy-4-(4-nitrophenyloxy)-butane is prepared.

By substitution of the reagents in Column A below in the above procedures, the compounds of Column B below are prepared.

| Column A | Column B |
| --- | --- |
| 2,4-dinitrophenol | 1,2-dihydroxy-3-(2,4-dinitrophenyloxy)-propane |
|  | 1,2-dihydroxy-4-(2,4-dinitrophenyloxy)-butane |
| 4-nitrophenol | 1,2-dihydroxy-3-(4-nitrophenyloxy)-propane |
|  | 1,2-dihydroxy-4-(4-nitrophenyloxy)-butane |
| fluorescein mono methyl ether | 1,2-dihydroxy-3-(fluorescein mono methyl ether)-propane |
|  | 1,2-dihydroxy-4-(fluorescein mono methyl ether)-butane |
| 7-hydroxy coumarin | 1,2-dihydroxy-3-(7-hydroxy coumarin)-propane |
|  | 1,2-dihydroxy-4-(7-hydroxy coumarin)-butane |
| 2,4-diiodo$^{125}$ phenol | 1,2-dihydroxy-3-(2,4-diiodo$^{125}$ phenol)-propane |
|  | 1,2-dihydroxy-4-(2,4-diiodo$^{125}$ phenol)-butane. |

EXAMPLE 3

A mixture of 1,2-dihydroxy-3-(4-nitrophenyloxy)propane (80 grams) in ethanol (400 milliliters) and a solution of ammonia (0.880) (400 ml.) is heated on the steam bath for 1 ½ hours. After allowing the mixture to cool the separated solids are collected and the mother liquors concentrated somewhat to remove ammonium hydroxide. After the addition of ethanol to remove turbidity, concentrated hydrochloric acid in equal volume is added to give 1-amino-2-hydroxy-3-(4'-nitrophenyloxy)-propane hydrochloride which can be purified from ethyl acetate-methanol. The foregoing solids, on crystallization from aqueous ethanol, furnish 1-amino-2-hydroxy-3-(4-nitrophenyloxy)-propane.

In like manner, the products of Example 2 are converted to the corresponding 1-amino compounds, that is
1-amino-2-hydroxy-3-(4-nitrophenyloxy)-propane,
1-amino-2-hydroxy-4-(4-nitrophenyloxy)-butane,
1-amino-2-hydroxy-3-(2,4-dinitrophenyloxy)-propane,
1-amino-2-hydroxy-4-(2,4-dinitrophenyloxy)-butane,
1-amino-2-hydroxy-3-(fluorescein mono methyl ether)-propane,
1-amino-2-hydroxy-4-(fluorescein mono methyl ether)-butane,
1-amino-2-hydroxy-3-(7-hydroxy coumarin)-propane,
1-amino-2-hydroxy-4-(7-hydroxy coumarin)-butane,
1-amino-2-hydroxy-3-(2,4-diiodo$^{125}$ phenol)-propane, and
1-amino-2-hydroxy-4-(2,4-diiodo$^{125}$ phenol)-butane.

EXAMPLE 4

Redistilled, cold 2,3-oxidopropanol (1.93 grams; 26.1 mmole) and 2,4-dinitrofluorobenzene (4.34 grams; 23.4 mmole) are combined with triethylamine (7 ml.) and kept at room temperature over night. The solid which forms is removed by filtration and dissolved into a small volume of chloroform. The chloroform solution is layered onto a column of silicic acid (5 × 50 cm) which is developed with chloroform and then with ethylacetate. The 1,2-oxido-3-(2,4-dinitrophenyloxy)-propane product is eluted with ethyl acetate and crystallized from ethyl acetate.

EXAMPLE 5

3-(2,4-Dinitrophenyloxy)-1,2-O-isopropylideneglycerol is prepared from 1,2-O-isopropylideneglycerol using dinitrofluorobenzene as set forth in Example 4.

The isopropylidene group is removed by treatment with 80% acetic acid for 17 hours at room temperature. After removal of the acetic acid by evaporation under reduced pressure, the oily residue is crystallized from benzene to yield 1,2-dihydroxy-3-(2,4-dinitrophenyloxy)propane.

Similarly, 1-amino-2-hydroxy-3-(2,4-dinitrophenyloxy)-propane and 1-amino-2-hydroxy-4-(2,4-dinitrophenyloxy)-butane are prepared.

EXAMPLE 6

To a solution of sodium 4-nitrophenolate (11 grams; 56 mmole) in dimethylformamide (50 ml.) is added 4-bromo-1-butene (5 g; 37 mmole). After 2.5 hours of heating at 100° C., the reaction mixture is diluted with 400 ml. of water and extracted with light petroleum ether. The ether extracts are re-extracted with cold 5% sodium hydroxide and then washed with water and dried over magnesium sulfate. This solution is evaporated under reduced pressure and the residual oil crystallized from petroleum ether at 0° to yield 4-(4-nitrophenoxy)-1-butene.

To a solution of the resultant compound (6.0 grams; 3 mmole) in benzene (150 ml.) is added m-chloroperbenzoic acid (9.0 g; 52 mmole). The mixture is shaken for 24 hours at 37° C. in the dark. After this time, the solvent is removed and the residue chromatographed on a silicic acid column (5 × 50 cm.) using chloroform containing 0.5% methanol as eluting solvent to obtain 1,2-oxido-4-(4-nitrophenoxy)-butane.

EXAMPLE 7

Hydrogen peroxide (1 milliliter; 30 percent) is added to a mixture of 4-(4-nitrophenoxy)-1-butene (1.0 g.) in formic acid (9 ml; 98%). After four days at room temperature, the pH of the reaction is brought to 9 with ammonium hydroxide and shaken to hydrolyze the intermediate formyl esters. The product is isolated by extracting this mixture with chloroform. The dried chloroform solution is evaporated and a solid obtained. Recrystallization from a small volume of chloroform gives 1,2-dihydroxy-4-(4-nitrophenyloxy)-butene. The 1,2-dihydroxy-4-(4-nitrophenyloxy)-butane is prepared from 1,2-oxido-4-(4-nitrophenoxy)-butane using the acid conditions reported above. The diol product is crystallized from chloroform.

EXAMPLE 8

To a solution of 1,2-O-isopropylidene-4-butanol (1.46 grams; 10 mmole) in triethylamine (5 ml.) is added 2,4-dinitrofluorobenzene (1.9 g.; 9.9 mmole). After 17 hours at room temperature, the solution is evaporated to a small volume, dissolved into chloroform and passed onto a silicic acid column (5 × 50 cm.). The column is eluted with chloroform giving an oil. The oil is treated with 80% acetic acid for 18 hours at room temperature. After removal of the acetic acid by evaporation, the residue is chromatographed on preparative silicic acid plates (10% methanol in chloroform) eluting with methanol to give 1,2-dihydroxy-4-(2,4-dinitrophenyloxy)-butane which can be crystallized from ether.

The above procedures are also useful for preparing the products of Examples 1 to 3.

EXAMPLE 9

The corresponding 1-mercapto-2-hydroxy compounds corresponding to those prepared above, are prepared by substituting sodium sulfide for the acid conditions in Example 7. The mercapto esters are prepared by reacting the 1,2-oxido compounds with, e.g. sodium thioacetate.

EXAMPLE 10

A solution of 5.83 grams (0.03 mmole) of 1-(4-nitrophenyloxy)-2,3-oxidopropane and 3.0 g. (0.03 mmole) of succinimide in 25 ml. of ethanol is treated with three drops of pyridine and then is refluxed for four hours. On cooling the reaction mixture to 0° C., separation of an oil is observed. The chilled mixture containing the separated oil is warmed to room temperature to give 1-[3-(4-nitrophenyloxy)-2-hydroxypropyl] succinimide.

The succinimide derivative prepared in the previous reaction (1.0 g., 3.6 mmole) is dissolved in a mixture of 10 ml. of 95% ethanol and 5 ml. of 12N hydrochloric acid. The solution is heated at reflux for six hours, and is left to stand at room temperature overnight. The solvent is distilled at reduced pressure, and the residue taken up in water and ether. The aqueous phase is separated, washed with ether, and evaporated to dryness. The residue semi-solid material is crystallized from ethanol/ether, to give 1-amino-3-(4-nitrophenyloxy)-2-propanol hydrochloride.

A solution of 232.5 mg. (1.0 mmole) of 3-(4-nitrophenyloxy)-1-amino-2-propanol hydrochloride, 420 mg. (1.0 mmole) of carbobenzoxy-1-phenylalanine, and 297 mg. (1.2 mmole) (N-carboethoxy-2-ethoxy-1,2-dihydroquinoline) in 10 ml. of pyridine is allowed to stand at room temperature for 24 hours. The solvent is removed under vacuum and the residual oil is dissolved in water and ethyl acetate. The aqueous phase is removed, and the ethyl acetate solution is washed twice with 1N hydrochloric acid, twice with 1M sodium carbonate, and once with saturated sodium chloride solution. The ethyl acetate solution is evaporated under vacuum and 2 ml. of 31% HBr in acetic acid is added to the residual material. The solvent is removed under vacuum, and the residue taken up in ether and dilute hydrochloric acid to give α-amino-N-[2-hydroxy-3-(4-nitrophenyloxy)propyl] hydrocinnamamide hydrobromide.

EXAMPLE 11

To a solution of 200 mg. (0.88 mmole) of 1,2-dihydroxy-4-(4-nitrophenyloxy)-butane and 200 mg. of (0.96 mmole) of N-carbobenzylglycine in 10 ml. of benzene is added two drops of concentrated sulfuric acid. The mixture is heated at reflux for one hour, allowed to cool, and the benzene solution washed successively with 1M sodium carbonate solution, water, 0.5M sodium periodate solution, and twice with water. The benzene is removed to leave a white solid which is crystallized from petroleum ether-ethyl acetate to give a 1,2-dihydroxy-4-(4-nitrophenyloxy)-butane 1-(N-carbobenzoxy)aminoacetate.

Seventy-two milligrams of the product is dissolved in 0.5 ml. of 31% HBr in acetic acid solution. The solution is shaken for 15 minutes with occasional mild heating on the steam bath. Ether is added to the solution and a precipitate appears. Extraction with water gives an aqueous phase containing 75% of the 4-nitrophenyloxy chromaphore used in the reaction. Evaporation of the solvent, and recrystallization from ethyl acetate-ethanol gives 3-(4-nitrophenyloxy)-2-hydroxypropyl glycerate hydrobromide.

The following examples illustrate the method by which the enzymatically hydrolyzable ester compounds hereof are prepared.

EXAMPLE 12

A solution of 15 milliliters of sodium acetate in glacial acetic acid (1M in sodium acetate) containing 1,2-oxido-3-(4-nitrophenyloxy)-propane (1.95 g; 10 mmole) is heated at 100° C. for 2 hours. The acetic acid is removed by evaporation and the residue is passed onto a silicic acid column (4 × 10 cm.) and eluted with chloroform containing 10% methanol. The sodium acetate free eluant is evaporated to dryness and chromatographed with silicic acid to yield 1-acetoxy-2-hydroxy-3-(4-nitrophenyloxy)-propane, 1-hydroxy-2-acetoxy-3-(4-nitrophenyloxy)-propane, and 1,2-diacetoxy-3-(4-nitrophenyloxy)-propane which can be crystallized from ethyl acetate-petroleum ether.

In like manner, the following compounds are prepared:
1-acetoxy-2-hydroxy-4-(4-nitrophenyloxy)-butane,
1-hydroxy-2-acetoxy-4-(4-nitrophenyloxy)-butane,
1,2-diacetoxy-4-(4-nitrophenyloxy)-butane,
1-acetoxy-2-hydroxy-3-(2,4-dinitrophenyloxy)propane,
1-hydroxy-2-acetoxy-3-(2,4-dinitrophenyloxy)-propane,
1,2-diacetoxy-3-(2,4-dinitrophenyloxy)-propane,
1-acetoxy-2-hydroxy-4-(2,4-dinitrophenyloxy)-butane,
1-hydroxy-2-acetoxy-4-(2,4-dinitrophenyloxy)-butane,
1,2-diacetoxy-4-(2,4-dinitrophenyloxy)-butane,
1-acetylamino-2-hydroxy-3-(4-nitrophenyloxy)-propane,
1-amino-2-acetoxy-3-(4-nitrophenyloxy)-propane,
1-acetylamino-2-acetoxy-3-(4-nitrophenyloxy)-propane,
1-acetylamino-2-hydroxy-3-(4-nitrophenyloxy)-butane,
1-amino-2-acetoxy-3-(4-nitrophenyloxy)-butane,
1-acetylamino-2-acetoxy-3-(4-nitrophenyloxy)-butane,
1-acetylamino-2-hydroxy-3-(2,4-dinitrophenyloxy)-propane,
1-amino-2-acetoxy-3-(2,4-dinitrophenyloxy)-propane,
1-acetylamino-2-acetoxy-3-(2,4-dinitrophenyloxy)-propane,
1-acetylamino-2-hydroxy-4-(2,4-dinitrophenyloxy)-butane,
1-amino-2-acetoxy-4-(2,4-dinitrophenyloxy)-butane,
1-acetylamino-2-acetoxy-4-(2,4-dinitrophenyloxy)-butane, and so forth.

Similarly, by use of an alternative carboxylic acid reagent, the other carboxylic acid esters hereof are prepared, for example, the propionates, valerates, octanoates, decanoates, tridecanoates, hexadecanoates, and octadecanoates, such as 1-propionyloxy-2-hydroxy-3-(4'-nitrophenyloxy)-propane, and so forth, 1-propionylamino-2-hydroxy-3-(4'-nitrophenyloxy)-propane, and so forth.

Use of the corresponding thio acid salts prepares the corresponding mercapto esters, e.g.
1-acetylthio-2-hydroxy-4-(4-nitrophenyloxy)-butane,
1-mercapto-2-acetoxy-4-(4-nitrophenyloxy)-butane,
1-acetylthio-2-acetoxy-4-(4-nitrophenyloxy)-butane,
1-acetylthio-2-hydroxy-3-(2,4-dinitrophenyloxy)-propane,
1-mercapto-2-acetoxy-3-(2,4-dinitrophenyloxy)-propane,
1-acetylthio-2-acetoxy-3-(2,4-dinitrophenyloxy)-propane,
1-acetylthio-2-hydroxy-4-(2,4-dinitrophenyloxy)-butane,
1-mercapto-2-acetoxy-4-(2,4-dinitrophenyloxy)-butane,
1-acetylthio-2-acetoxy-4-(2,4-dinitrophenyloxy)-butane,
1-acetylthio-2-hydroxy-3-(4-nitrophenyloxy)-propane,
1-mercapto-2-acetoxy-3-(4-nitrophenyloxy)-propane,
1-acetylthio-2-acetoxy-3-(4-nitrophenyloxy)-propane,
and so forth.

Similarly, by use of an alternative carboxylic acid reagent, the other carboxylic acid esters hereof are prepared, for example, the propionates, valerates, octanoates, decanoates, tridecanoates, hexadecanoates, and octadecanoates, such as 1-propionylthio-2-hydroxy-3-(4-nitrophenyloxy)-propane, and so forth, 1-propionylthio-2-hydroxy-4-(4-nitrophenyloxy)-butane, and so forth.

EXAMPLE 13

An aqueous solution of dibasic potassium phosphate (10 ml., 0.5M) and 1,2-oxido-3-(4-nitrophenyloxy)-propane (0.5 mmole, 98 mg.) is refluxed for 17 hours, then diluted to 100 ml. and passed onto a column of DEAE-Sephadex (3 × 25 cm.). A linear gradient of triethylammonium bicarbonate (500 ml., 0.01M, pH 7.5 in the mixing vessel and 500 ml. of 0.75M in the reservoir) is the eluant to yield 1-phosphato-2-hydroxy-3-(4-nitrophenyloxy)-propane, 1-hydroxy-2-phosphato-3-(4-nitrophenyloxy)-propane, and 1,2-diphosphato-3-(4-nitrophenyloxy)-propane as their triethylammonium salts.

A solution of 1,2-dihydroxy-3-(4-nitrophenyloxy)-propane (1 mmole) in dry pyridine (3 ml.) containing β-cyanoethylphosphate (1.5 mmole, pyridinium salt) and dicyclohexylcarbodiimide (0.35 g.) is kept at room temperature for two days. Water is added and after 2 hours the solution is filtered. The filtrate is evaporated to dryness and redissolved into 5M ammonium hydroxide. After 1.5 hours at 60° C., the solution is evaporated and the residue placed on a DEAE-Sephadex column (2.5 × 25 cm.). The column was eluted as described above. After lyophilization, 1-phosphato-2-hydroxy-3-(4-nitrophenyloxy)-propane, 1-hydroxy-2-phosphato-3-(4-nitrophenyloxy)-propane, and 1,2-diphosphato-3-(4-nitrophenyloxy)-propane products are obtained as their triethylammonium salts.

Similarly, the following phosphate esters are prepared:
1-phosphato-2-hydroxy-4-(4-nitrophenyloxy)-butane,
1-hydroxy-2-phosphato-4-(4-nitrophenyloxy)-butane,
1,2-diphosphato-4-(4-nitrophenyloxy)-butane,
1-phosphato-2-hydroxy-3-(2,4-dinitrophenyloxy)-propane,
1-hydroxy-2-phosphato-3-(2,4-dinitrophenyloxy)-propane,
1,2-diphosphato-3-(2,4-dinitrophenyloxy)-propane,
1-phosphato-2-hydroxy-4-(2,4-dinitrophenyloxy)-butane,
1-hydroxy-2-phosphato-4-(2,4-dinitrophenyloxy)-butane,
1,2-diphosphato-4-(4-nitrophenyloxy)-butane,
1-phosphatamino-2-hydroxy-3-(4-nitrophenyloxy)-propane, 1-amino-2-phosphato-3-(4-nitrophenyloxy)-propane,
1-phosphatamino-2-phosphato-4-(4-nitrophenyloxy)-propane,
1-phosphatamino-2-hydroxy-4-(4-nitrophenyloxy)-butane,
1-amino-2-phosphato-4-(4-nitrophenyloxy)-butane,
1-phosphatamino-2-phosphato-4-(4-nitrophenyloxy)-butane,
1-phosphatamino-2-hydroxy-3-(2,4-dinitrophenyloxy)-propane,
1-amino-2-phosphato-3-(2,4-dinitrophenyloxy)-propane,
1-phosphatamino-2-phosphato-3-(2,4-dinitrophenyloxy)-propane,
1-phosphatamino-2-hydroxy-4-(2,4-dinitrophenyloxy)-butane,
1-amino-2-phosphato-4-(2,4-dinitrophenyloxy)-butane,
1-phosphatamino-2-phosphato-4-(2,4-dinitrophenyloxy)-butane, and so forth.

EXAMPLE 14

To a solution of dimethylformamide and concentrated sulfuric acid (2 ml; 3:1 v/v) is added 1,2-oxido-3-(4'-nitrophenoxy)-propane (195 mg; 1 mmole). After one hour at room temperature, ice water (20 ml.) is added and the solution neutralized with ammonium hydroxide. The product is purified either by preparative chromatography on Whatman 3mm. paper in Solvent C or by chromatography on DEAE-Sephadex. For column chromatography the reaction solution is diluted to 100 ml. with water, and passed onto a DEAE-Sephadex column (50 × 4 cm.). After washing the column with five to six bed volumes of water, the column is eluted using a gradient of triethylammonium bicarbonate (500 ml. of 0.75M salt in the reservoir pH 7.5 and 500 ml. of water in the mixing vessel). The sulfate ester is eluted between 0.01 to 0.1M triethylammonium bicarbonate. The fractions of this peak are combined and lyophilized to yield the 1-sulfato-2-hydroxy-3-(4-nitrophenyloxy)-propane, 1-hydroxy-2-sulfato-3-(4-nitrophenyloxy)-propane, 1,2-disulfato-3-(4-nitrophenyloxy)-propane products as their triethylammonium salts.

1,2-Dihydroxy-4-(4-nitrophenyloxy)-propane (1 mmole) is dissolved in cool, dry dimethylformamide (6 ml.) containing dicyclohexylcarbodiimide (0.41 g; 2 mmole). To this is added an ice cold solution of sulfuric acid (1.1 mmole) in dry dimethylformamide (5 ml.). After 15 minutes, the precipitated dicyclohexylurea is removed by filtration and the filtrate evaporated to an oil. Water (100 ml.) is added to the residue, and this solution is passed onto a column of DEAE-Sephadex (2.5 × 25 cm.). The column is developed using the conditions described above except the gradient is from 0.01 to 0.5M triethylammonium bicarbonate. The sulfate esters are obtained between 0.01 to 0.1M triethylammonium bicarbonate and are isolated as their triethylammonium salts.

Similarly, the following sulfate esters are prepared:
1-sulfato-2-hydroxy-4-(4-nitrophenyloxy)-butane,
1-hydroxy-2-sulfato-4-(4-nitrophenyloxy)-butane,
1,2-disulfato-4-(4-nitrophenyloxy)-butane,
1-sulfato-2-hydroxy-3-(2,4-dinitrophenyloxy)-propane,
1-hydroxy-2-sulfato-3-(2,4-dinitrophenyloxy)-propane,
1,2-disulfato-3-(2,4-dinitrophenyloxy)-propane,
1-sulfato-2-hydroxy-4-(2,4-dinitrophenyloxy)-butane,
1-hydroxy-2-sulfato-4-(2,4-dinitrophenyloxy)-butane,
1,2-disulfato-4-(2,4-dinitrophenyloxy)-butane,
1-sulfatamino-2-hydroxy-3-(4-nitrophenyloxy)-propane,
1-amino-2-sulfato-3-(4-nitrophenyloxy)-propane,
1-sulfatamino-2-sulfato-3-(4-nitrophenyloxy)-propane,
1-sulfatamino-2-hydroxy-3-(4-nitrophenyloxy)-butane,
1-amino-2-sulfato-3-(4-nitrophenyloxy)-butane,
1-sulfatamino-2-sulfato-3-(4-nitrophenyloxy)-butane,
1-sulfatamino-2-hydroxy-3-(2,4-dinitrophenyloxy)-propane,
1-amino-2-sulfato-3-(2,4-dinitrophenyloxy)-propane,
1-sulfatamino-2-sulfato-3-(2,4-dinitrophenyloxy)-propane,
1-sulfatamino-2-hydroxy-4-(2,4-dinitrophenyloxy)-butane,
1-amino-2-sulfato-4-(2,4-dinitrophenyloxy)-butane,
1-sulfatamino-2-sulfato-4-(2,4-dinitrophenyloxy)-butane.

EXAMPLE 15

N-benzoyl-L-phenylalanine amino acid (2 mmoles) is dissolved in dry dimethylsulfoxide (DMSO 1 ml.) containing triethylamine (2 mmoles) and 1,2-epoxy-3-(p-nitrophenoxy)-propane (2 mmoles) is then added thereof. The solution is heated on a steam bath with exclusion of moisture until tlc (benzene-acetone 9:1 or 4:1) indicates all the epoxide has reacted to products with much lower $R_f$ (reaction time three to four hours). After evaporation of the DMSO in high vacuo the residue is chromatographed on silica gel (0.05–0.2mm, 70–325 mesh ASTM, 100 g.) with benzene-acetone 4:1 to give the N-benzoyl-L-phenylalanine 4-(4-nitrophenyloxy)-2-hydroxy-n-butyl ester.

In a similar manner, N-carbobenzoxy-L-phenylalanine 3-(4-nitrophenyloxy)-2-hydroxy-n-propyl ester, N-carbobenzoxy-L-glycine-4-(p-nitrophenoxy)-2-hydroxy-n-butyl ester, N-t.-butoxycarbonyl-L-tyrosine 3-(p-nitrophenoxy)-2-hydroxy-n-propyl ester, and N-t-butoxycarbonyl-L-tyrosine 4-(p-nitrophenoxy)-2-hydroxy-n-butyl ester are prepared.

The N-carbobenzoxy-L-glycine-4-(p-nitrophenoxy)-2-hydroxy-n-butyl ester (1 mmole) is dissolved in 5 ml. of trifluoroacetic acid (TFA), the flask tightly stoppered, and kept overnight at 30°–40° C. (bath temperature). The reaction mixture is evaporated to dryness at a temperature <40° and last traces of TFA removed by two co-evaporations with added absolute ethanol toluene. The glycine 3-(4-nitrophenyloxy)-2-hydroxy-n-propyl ester tetrafluoroacetate crystallizes upon trituration with absolute ethanol which can be recrystallized from ethanol-ether.

Evaporation with 1N hydrochloride affords the glycine-3-(4-nitrophenyloxy)-2-hydroxy-n-propyl ester hydrochloride.

The crude L-phenylalanine-3-(4-nitrophenyloxy)-2-hydroxy-n-propyl ester tetrafluoroacetate (ca. 400 mg.), prepared as described above, is dissolved in 40 ml. of 80% MeOH and is applied on top of a Dowex-50 (H+) column (15 × 2 cm) which has been equilibrated with 80% MeOH. The column is first washed with ca. 500 ml. of MeOH, then with 100 ml. 0.01N HCl in 80% MeOH and the product eluted with 0.2N hydrochloride in 80% MeOH, the elution being monitored by a UV analyzer. The fractions containing the product are pooled, evaporated to dryness (temperature <40°), most of the excessive hydrochloride removed by repeated co-evaporations with H₂O and the oily residue crystallized by trituration with absolute ethanol. Recrystallization from ethanol-ether gives L-phenylalanine 3-(4-nitrophenyloxy)-2-hydroxy-n-propyl ester hydrochloride.

The N-t.-butoxycarbonyl-L-tyrosine 3-(p-nitrophenoxy)-2-hydroxy-n-propyl ester (500 mg.) in trifluoroacetic acid (6 ml.) are allowed to stand at room temperature for one hour. Evaporation of the trifluoroacetic acid gives a white foam, homogenous on tlc. The trifluoroacetates are converted to the hydrochlorides by two evaporations with added hydrochloride (1 ml. 1N hydrochloride) tyrosine 3-(4-nitrophenyloxy)-2-hydroxy-n-propyl ester hydrochloride is recrystallized from ethyl acetate and recrystallized from ethanol-ether.

Tyrosine 3-(4-nitrophenyloxy)-n-butyl ester hydrochloride is obtained crystalline from $H_2O$ and recrystallized from ethanol-ether.

The following examples illustrate the method of measuring enzymatic activity in biological material.

EXAMPLE 16

Purified *E.coli* alkaline phosphomonoesterase enzyme (10 μl; 1.15 mg/ml.) is added to a solution of the 1-phosphato-2-hydroxy-4-(4-nitrophenyloxy)-butane (7 mole/ml.) substrate in sodium bicarbonate buffer (0.1M; pH 8.0) which is equiliberated at 23°. At intervals, aliquots (0.4 ml.) are removed and added to an oxidizing solution (0.6 ml.) at 50°. The oxidizing solution contains methylamine hydrochloride (2.7M) and sodium periodate (0.01M) in potassium phosphate buffer (0.1M; pH 7.5). For each aliquot analysis, after five minutes in the oxidizing solution at this temperature, the optical density of the solution is read at 400 mμ against a control solution containing all the reagents except the enzyme, using molar extinction values of 11,200 at 318 mμ for substrate. The recovery of 4-nitrophenolate ion as measured spectrophotometrically is essentially theoretical when assayed after 21 hours.

Similar results are obtained when using 1-phosphato-2-hydroxy-4-(2,4-dinitrophenyloxy)-butane with this enzyme and for both substances with wheat germ acid phosphomonoesterase.

EXAMPLE 17

To a solution of sodium carbonate/bicarbonate (1.0 mμ; pH 9.0; 0.1M) containing 1-phosphato-2-hydroxy-4-(4'-nitrophenyloxy)-butane (ammonium salt 3.0 mmoles) is added 0.01 mμ of alkaline phosphomonoesterase (1 mg/ml. salt fractionated *Worthington Biochemistry* Freehold, N.J.). After a given interval in minutes, 0.1 ml. of the reaction is removed and added to a solution of sodium metaperiodate (0.4 ml; 0.025M 37). After approximately two minutes, sodium hydroxide (0.5 ml; 0.2M) is added and the absorbancy of the 4-nitrophenyloxy is determined at 400 mμ. The reaction is zero order for at least the first 20 minutes, and 50 mmoles of substrate is hydrolyzed per minute, per mg. of protein per ml. of reaction solution. The color measured is proportional to the amount of enzyme added.

EXAMPLE 18

Substrate solutions are prepared containing 100 mmole/ml. methanol of one of L-glycine 3-(4-nitrophenyloxy)-2-hydroxy-n-propyl ester, L-tyrosine 3-(4-nitrophenyloxy)-2-hydroxy-n-propyl ester, L-tyrosine 4-(4-nitrophenyloxy)-2-hydroxy-n-butyl ester, and L-phenylalanine 3-(4-nitrophenyloxy)-2-hydroxy-n-propyl ester.

Enzyme solutions are prepared at the following concentrations: 2.5 mg. α-chymotrypsin/25 ml. 0.001N HCl; 2.5 mg. trypsin/25 ml. 0.001N HCl; 2.5 mg. pepsin/25 ml. 0.1M sodium acetate pH 4.5; 2.5 mg. pepsin/25 ml. water; 2.5 mg. panprotease/25 ml. water; 2.5 mg. pronase/25 ml. water.

Esterase activity is determined by mixing 0.1 ml. of the substrate solution with 0.8 ml. phosphate buffer (0.05M, pH 6) and equilibrating the mixture at 37° C. Then, 0.1 ml. of the enzyme solution at 37° C. is added at time intervals, aliquots (0.1 ml. or 0.05 ml.) are removed and pipetted into a cuvette containing sodium acetate (6 or 6.5 ml) and periodate (0.05 ml.) and assayed as described below. The control contained 0.001N hydrochloride (0.1 or 0.05 ml.) instead of the enzyme solution and is incubated in exactly the same manner as the sample.

0.1 Milliliters from the enzymatic reaction is pipetted into a 1 ml. cuvette containing 0.6 ml. (or 0.65 ml.) sodium acetate buffer (0.1M, pH 4.5) and 0.05 ml. sodium meta periodate (0.1M). After 5 minutes in a water bath at 50°, 0.05 ml. aqueous ethylene glycol (0.2M) is added and the cell kept another 5 minutes at 50° C. The excessive periodate is reduced quantitatively before the solution is rendered alkaline. After the reduction, 0.2 ml. (total volume 1 ml.) methylamine hydrochloride (ca. 6M, pH 0.5) is added and the absorbance at λ = 400 mμ measured after five minutes (in the case of the propane diol esters after 25 minutes at 50°). The blank contains everything but the enzyme and is incubated in the same way as the sample cuvette. An absorbance of 1.80 corresponds to 0.1 mmole of the amino ester/ml. ($\lambda_{max}^{Methylamine\,pH\,9.5}$ of p-nitrophenolate = 400 mμ, ε = 18,000), indicating the hydrolysis of 0.1 mmole amino acid ester by the enzyme.

The above experiments indicate L-glycine 3-(4-nitrophenyloxy)-n-propyl ester are good to excellent substrates of α-chymotrypsin and trypsin at pH 6. In addition, the tyrosine 3-(4-nitrophenyloxy)-n-propyl ester is also a good substrate for pan-protease and pronase.

EXAMPLE 19

Substrate solutions are prepared of 2-hydroxy-4-(p-nitrophenoxy)-N-(L-tyrosyl)-1-butylamine and 2-hydroxy-3-(p-nitrophenoxy)-N-(L-phenylalanyl)-1-propylamine containing ca. 20 mmole per ml. 0.01M phosphate buffer pH 6, 7, 8 and 9. In the case of the 2-hydroxy-4-(p-nitrophenoxy)-N-(N'-acetyl-L-tyrosyl)-1-butylamine and N-acetyl-L-tyrosine 2-hydroxy-4-(p-nitrophenoxy)-n-butyl ester saturated solutions are used, the respective solubility thereof in 0.01M phosphate buffers being in the order of 1 mmole per ml. decreasing at higher pH.

To 1 ml. substrate solution at 37° is pipetted 10λ of a solution of the enzyme in 0.001N HCl, equilibrated also at 37°, and after incubation at 37°, aliquots are removed and assayed at certain time intervals.

The assay procedure is carried out in the following way: 0.1 ml. of the enzymatic reaction is pipetted into a 1 ml. cuvette containing 0.2 ml. of solution I (solution I = 0.1M sodium acetate - 0.01M $NaIO_4$, 1:1), after 5 minutes in a water bath at 50°, 0.7 ml. of solution II is added (solution II = 0.2M ethyleneglycol - ca. 2.5M methylamine, adjusted to pH 9.5 with HCl, 1:6) and the absorbance at λ=400 mμ is measured either after 5 minutes or after 25 minutes, depending upon the substrate employed.

(a) In the case of amino acid esters of 4-(p-nitrophenoxy)-1,2-butanediol or amino acid amides of 4-(p-nitrophenoxy)-2-hydroxyl-1-butylamine, the elimination of p-nitrophenolate is quantitative within five minutes at room temperature, therefore, the absorbance is measured 5 minutes after the addition of solution II.

(b) In the case of amino acid esters of 3-(p-nitrophenoxy)-1,2-propanediol or amino acid amides of 3-(p-nitrophenoxy)-2-hydroxy-1-propylamine, the cuvette is kept at 50° for 25 minutes before measuring the absorbance at $\lambda = 400$ to ensure a fairly well reproducible 50% elimination of p-nitrophenolate.

The blank contains everything the sample cuvette contains except 0.001N HCl instead of the enzyme solution. The calculations are based on an extinction coefficient of 18,000, found for p-nitrophenolate in ca. 2M methylamine, pH 9.5.

The above experiments indicate the amino acid amides of 2-hydroxy-4-(p-nitrophenoxy)-1-butylamine and 2-hydroxy-3-(p-nitrophenoxy)-1-propylamine respectively are hydrolyzed by several proteolytic enzymes, namely α-chymotrypsin, pan protease, pronase and peptidase at a low rate. The 2-hydroxy-4-(p-nitrophenoxy)-N-(N'-acetyl-L-tyrosyl)-1-butylamine is hydrolyzed by α-chymotrypsin with a $k_o = 0.0093$ mmoles/min. per mg. enzyme/ml. Esters of α-amino acids with an α-OH in the alcohol portion are, in general, very easily hydrolyzed at pH values around 7. The N-acetyl-L-tyrosine 2-hydroxy-4-(p-nitrophenoxy)-n-butyl ester is an active substrate for α-chymotrypsin and other proteolytic enzymes.

The following example illustrates the method by which periodate concentrations can be measured.

EXAMPLE 20

Two exactly similar solutions containing periodate are prepared. The "initial" solution is used to determine the periodate initially present and the "reaction" solution is used to determine the amount of periodate present after the oxidation reaction on the unknown. The unknown is added to the "reaction" solution and after the oxidation is complete, 1,2-dihydroxy-4-(4-nitrophenyloxy)-butane is added to both the "initial" and "reaction" solutions. After 15 minutes, a basic buffer is added to both and after 5 minutes their color is determined at 400 mμ. The amount of 1-phosphato-2-hydroxy-4-(4'-nitrophenyloxy)-butane added is about three times the amount of periodate in the "initials" solution and the amount of periodate in this solution is sufficient to give about 0.8 $A_{400}$ units after treatment with the basic buffer. The amount of periodate consumed by the unknown sample is the difference between the "initial" $A_{400}$ reading and the "reaction" $A_{400}$ reading divided by the molar extinction value of 4-nitrophenolate ion.

This procedure is followed with adenosine 5'-phosphate as the unknown as an aqueous solution of adenosine 5'-phosphate (0.0488M; sodium salt), and an aqueous solution of 1,2-dihydroxy-4-(4'-nitrophenyloxy)-butane (0.013M) and molar extinction values of $\epsilon = 1.12 \times 10^4$ at 318 mμ for 1,2-dihydroxy-4-(4'-nitrophenyloxy)-butane and aqueous sodium periodate (0.0518M), and determining the concentration of periodate ion using an $\epsilon$ at 157.9 at 300 mμ in acetate buffer (1M; pH 4.3).

To 0.8 ml. of the "initial" and "reaction" solution is added 0.2 ml. of 1,2-dihydroxy-4-(4'-nitrophenyloxy)-butane in solution. After 15 minutes an aliquot (0.05 ml.) of this mixture is added to sodium bicarbonate-carbonate buffer (0.95 ml, 0.1M, pH 9.5). After 5 minutes at 50° C., this solution is read at 400 mμ with a control which contains no periodate. The "initial" reading is 0.85 and the "reaction" is 0.465. The difference, 0.385 divided by the molar extinction value of p-nitrophenolate ion, 1.64 $\times$ $10^4$, is 2.3 $\times$ $10^{-5}$M giving an analysis of 96% of theory.

When repeated using 1,2-dihydroxy-4-(2,4-dinitrophenyloxy)-butane and a molar extinction value $\epsilon = 9.5 \times 10^3$ at 301 mμ, similar results are obtained.

Similarly, this method is used to determine D-arabitol and D-glucose concentration and glycol content in ribonuclei acids and with triglycerides, such as tripalmitin, with similar results in each instance.

What is claimed is:

1. A reagent useful for enzyme measurements which is a compound selected from those represented by the following formula:

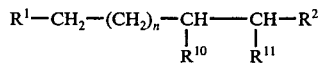

wherein,
$R^1$ is 4-nitrophenyloxy or 2,4-dinitrophenyloxy;
$n$ is 1;
$R^2$ is hydrogen; and
$R^{10}$ and $R^{11}$ each is independently hydroxy or a carboxylic ester of the formula

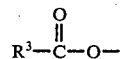

wherein $R^3$ is alkyl of one to eighteen carbon atoms, provided that at least one of $R^{10}$ and $R^{11}$ is a carboxylic ester.

2. The compound according to claim 1 wherein said carboxylic ester is acetoxy.

3. The compound according to claim 2 wherein $R^{11}$ is acetoxy, $R^{10}$ is hydroxy, and $n$ is 1.

* * * * *